United States Patent
Nalewajek et al.

(10) Patent No.: US 8,268,063 B2
(45) Date of Patent: Sep. 18, 2012

(54) CARRIER SOLVENT FOR FINGERPRINT FORMULATIONS

(75) Inventors: David Nalewajek, West Seneca, NY (US); Cheryl L. Cantlon, Clarence Center, NY (US); Andrew J. Poss, Kenmore, NY (US); Rajiv Ratna Singh, Getzville, NY (US); Ian Shankland, Randolph, NJ (US)

(73) Assignee: Honeywell International Inc., Morristown, NJ (US)

( * ) Notice: Subject to any disclaimer, the term of this patent is extended or adjusted under 35 U.S.C. 154(b) by 775 days.

(21) Appl. No.: 12/422,260

(22) Filed: Apr. 11, 2009

(65) Prior Publication Data

US 2009/0269478 A1    Oct. 29, 2009

Related U.S. Application Data

(60) Provisional application No. 61/044,873, filed on Apr. 14, 2008.

(51) Int. Cl.
*C09D 11/00* (2006.01)
(52) U.S. Cl. .................. 106/31.32; 106/31.58
(58) Field of Classification Search .......... 106/31.32, 106/31.58
See application file for complete search history.

(56) References Cited

U.S. PATENT DOCUMENTS 6,592,929 B1  7/2003  Berka et al.
2008/0020126 A1  1/2008  Arndt

FOREIGN PATENT DOCUMENTS

JP    2003-061937 A    4/2003

OTHER PUBLICATIONS

English Machine Translation of JP 2003-061937.*
Ruhemann et al., Journal of Chem. Soc., vol. 97, pp. 1438-1449 (1910). US.
Svante Oden et al., Nature (Journal), Detection of Fingerprints by the Ninhydrin Reaction, vol. 173, pp. 449-450 (Mar. 6, 1954). US.
Pounds et al., Journal of Forensic Sciences, The Use of 1,8-Diazafluoren-9-one (DFO) for the Fluorescent Detection of Latent Fingerprints on Paper, vol. 35, Issue1, pp. 169-175 (1990). US.
Gardener et al., Journal of Forensic Sciences, Optimization and Initial Evaluation of 1,2-Indandione as a Reagent for Fingerprint Detection, vol. 48, Issue 6, pp. 1-5, (2003). US.
Champod et al., CRC Press, "Fingerprints and Other Ridge Skin Impressions," 1st Ed., pp. 128-131 (2004) US.
Hewlett et al., Journal of Forensic Identification, vol. 49, No. 4, p. 338 (1999). US.

* cited by examiner

*Primary Examiner* — Melvin C Mayes
*Assistant Examiner* — Veronica F Faison
(74) *Attorney, Agent, or Firm* — Bruce O. Bradford

(57) ABSTRACT

A method and composition for transforming a latent physiological biometric into a visible physiological biometric are provided, the method comprising: providing a latent biometric disposed on a surface of an article, wherein said biometric comprises at least one eccrine-derived compound; contacting said latent biometric with a developing solution, wherein said developing solution comprises at least one imaging reagent selected from ninhydrin and 1,8-diazafluoren-9-one and a carrier solvent comprising at least one $C_3$-$C_4$ hydrofluorocarbon; and reacting said imaging reagent with said eccrine-derived compound to produce a visible physiological biometric.

21 Claims, No Drawings

US 8,268,063 B2

CARRIER SOLVENT FOR FINGERPRINT FORMULATIONS

CROSS-REFERENCE TO RELATED APPLICATIONS

This application claims the priority benefit of U.S. Provisional Application No. 61/044,873, filed Apr. 14, 2008, which is incorporated herein by reference.

BACKGROUND

1. Field of the Invention

The present invention relates to compositions and method for detecting latent biological markers. More specifically, this invention relates to latent fingerprint detection formulations comprising organic solvents.

2. Description of Prior Art

Fingerprints can be used to link a criminal suspect to a crime and, therefore, are one of the most valuable pieces of evidence that can be gathered at a crime scene. Fingerprints generally are classified into three categories: visible, impression and latent. While visible and impression prints can be readily seen with the unaided eye and can be documented by photography, latent fingerprints are visually undetectable without the aide of chemical, physical, or electrical processing techniques. Most latent fingerprints are invisible deposits of natural secretions of skin on the surface of an article which typically occur as impressions corresponding to the friction ridges of the skin. These secretions, which are produced by the eccrine glands, typically comprise water, soluble amino acids, peptides, salts, lipids, and the like. It is possible to transform these deposits into a visibly detectable image. When the impressions form patterns that correspond to the unique friction ridges of a person's finger, palm, etc, the latent fingerprint can be useful in dactyloscopy.

To visibly detect and analyze latent fingerprints, the residue must be processed, preferably by developing a composition comprising an imaging reagent in a carrier solvent. For example, ninhydrin, which was discovered in 1910 [Ruhemann et al., *J. Chem. Soc.* 1910, 97, 1438-49], has long been used to detect latent fingerprints [Oden et al., *Nature*, 1954, 173, 449]. More recently, other compounds, such as 1,8-diazafluoren-9-one (DFO) and 1,2-indanedione, have been used as imaging reagents for developing latent fingerprints [see, e.g., Pounds, et al., *J. For. Sci.*, 1990, 35 (1), 169-175 and Gardener et al. *J. For. Sci.*, 2003, 48 (6), 1-5]. Both of these imaging reagents react with the amino acids and amines derived from peptides and/or proteins (e.g., terminal amines or lysine residues) present in eccrinal secretions to produce a dye that is visually detectable. Ninhydrin, in particular, degrades amino acids into aldehydes, ammonia, and $CO_2$ through a series of reactions. A portion of the ninhydrin is reduced into hydrindantin. A portion of the remaining ninhydrin condenses with ammonia and hydrindantin to produce an intensely blue or purple pigment, also known as Ruhemann's purple. Accordingly, when an eccrine residue exists in a pattern, such as the ridges corresponding to a fingerprint, this pigment renders the otherwise latent fingerprint into a visually detectable image. DFO also interacts with amino acids in eccrine residue to produce pale pink image. This observation image can be enhanced by using 560-620 nm light since the DFO-amino acid complex is strongly luminescent [Champod et al., "Fingerprints and Other Ridge Skin Impressions" 1st edition, CRC Press, 2004, 128-131].

In addition to an imaging reagent, such as ninhydrin or DFO, developing compositions typically include a carrier solvent. For example, certain ninhydrin formulations have used 1,1,2-trichlorotrifluoroethane (CFC-113) as a carrier solvent. [Hewlett et al., *J. For. Identification*, 1999, 49 (4), 338]. However, due to its negative impact on the earth's ozone layer, CFC-113 is no longer used commercially.

Hydrochlorofluorocarbons ("HCFCs"), such as 1,1-dichloro-1-fluoroethane (HCFC-141b), are also useful as carrier solvents in certain applications but have a lower ozone depletion potential (ODP) compared to CFCs. Therefore, HCFCs are used commonly as replacements for CFC carrier solvents. However, these types of compounds are also now being phased out of commercial use due to their relatively high Global Warming Potential (GWP).

While hydrofluorocarbons (HFCs) generally possess a lower GWP compared to HCFCs, identifying HFC replacement compounds that are suitable as a carrier solvent for imaging reagents is difficult. For example, HFC-4310mee has been studied as a potential replacement carrier solvent, but this compound possesses a relatively high GWP (=1500 relative to $CO_2$) and is not effective as a carrier solvent for DFO. [Hewlett et al.]

Accordingly, there remains a need to identify carrier solvents suitable as a replacement for CFCs and HCFCs that would not have the limitations and environmental shortcomings attributed to these materials.

SUMMARY OF THE INVENTION

Applicants have found that $C_3$-$C_4$ hydrofluorocarbons can be effectively used as carrier solvents in compositions used to detect latent fingerprints and other biometrics. In particular, Applicants have found that these carrier solvents generally have an ozone depletion value close to zero; have low global warming potential (e.g., below 1000); are volatile, non-toxic, and non-flammable; exhibit sufficient solubility for chemical reagents capable of imaging eccrinal residues; and are relatively non-polar to allow for proper development of the fingerprints for image capture.

Accordingly, provided is a composition comprising at least one imaging reagent selected from the group consisting of ninhydrin, hydrindantin, 1,8-diazafluoren-9-one, 1,2-indanedione, and derivatives thereof dissolved in a carrier solvent comprising at least one $C_3$-$C_4$ hydrofluorocarbon, preferably pentafluoropropane or pentafluorobutane.

According to another aspect of the invention, provided is a method for producing a visibly detectable image of a latent physiological biometric comprising (a) contacting a latent biometric deposited on a surface of an article with a developing composition, wherein said biometric comprises a pattern of residue derived from an eccrenial gland and said developing composition comprises a solution comprising at least one imaging reagent selected from the group consisting of ninhydrin, 1,8-diazafluoren-9-one, and 1,2-indanedione in a carrier solvent comprising at least one $C_3$-$C_4$ hydrofluorocarbon; and (b) reacting said imaging reagent with said residue to produce a dye, wherein said dye forms a visually detectable image corresponding to at least a portion of said pattern.

DETAILED DESCRIPTION OF PREFERRED EMBODIMENTS OF THE INVENTION

In a preferred embodiment of the present invention, the developing composition comprises a $C_3$-$C_4$ hydrofluorocarbon carrier solvent and an imaging reagent capable of rendering visual images of a latent biometric.

As used herein, the term "biometric" means a physiological deposit produced by a person, wherein the deposit is related to the shape, form, and/or pattern of dermal ridges of a person's skin, for example a fingerprint, palm geometry, foot print, toe print, and the like. Preferred biometrics include those that produce a unique or rarely occurring mark that can be associated with an individual, such as fingerprints. Examples of physiological deposits include residues derived from natural secretions of the eccrine gland present on friction ridge skin. Such residues typically comprise water and one or more organic compounds such as soluble amino acids, peptides, salts, lipids, and the like. Specific organic compounds include alanine, asparagine, aspartic acid, cysteine, glutamic acid, glutamine, glycine, proline, serine and tyrosine.

As used herein, the term "latent", with respect to biometric, means an invisible impression of a portion of a person's body that results from the person contacting the surface of an object and the term "invisible" means visually imperceptible without the aid of a device or developing process.

Preferred $C_3$-$C_4$ hydrofluorocarbons are of general formula:

$$C_nH_mF_z$$

where n is selected from the group consisting 2-4, m is selected from the group consisting of 1-4, and is selected from the group consistent with the formula z=(2n+2)−m provided that the GWP value of the hydrofluorocarbon is not more than 1000 relative to $CO_2$. Examples of $C_3$-$C_4$ hydrofluorocarbons useful with this invention include: pentafluoropropane, such as 1,1,1,3,3-pentafluoropropane and 1,1,2,2,3-pentafluoropropane; hexafluoropropane, such as 1,1,1,3,3,3-hexafluoropropane; heptafluoropropane, such as 1,1,1,2,3,3,3-heptafluoropropane; pentafluorobutane, such as 1,1,1,3,3-pentafluorobutane. Carrier solvents may also comprise mixtures of two or more of these. Preferred hydrofluorocarbons include isomers of pentafluoropropane, $C_3H_3F_5$. Preferred isomers include 1,1,2,2,3-pentafluoropropane (HFC-245ca) and 1,1,1,3,3-pentafluoropropane (HFC-245fa), with HFC-245fa being more preferred. HFC-245fa has a calculated GWP value of 950 while HFC-245ca has a calculated GWP value of 640.

Also contemplated for use in this invention are isomers of pentafluorobutane, $C_4H_5F_5$. While many isomers of pentafluorobutane are possible, the most preferred isomer for use in this invention is 1,1,1,3,3-pentafluorobutane (HFC-365mfc). HCF-365mfc has a calculated GWP value of 890.

It is also contemplated that the carrier solvent may include one or more hydrofluorocarbon co-solvents. Preferably, co-solvents are selected to gain one or more of the following advantages: increasing solubility of the latent fingerprint imaging reagent, decreasing the GWP value of the co-solvent, and minimizing the use of a more expensive imaging reagent, for example, where the more costly carrier solvent imparted the desired solubility as compared to the co-solvent in use. Co-solvents for use with this invention include mixtures of pentafluoropropanes and pentafluorobutanes. Particularly suitable for this application are co-solvent mixtures derived from HFC-245fa and HFC-365mfc. Such mixtures range from about 1 part to about 99 parts by weight HFC-245fa with the corresponding values for HFC-365mfc ranging from 99 parts to 1 part.

The solutions of the present invention can involve an azeotrope or azeotropic-like mixture of the hydrofluorocarbon with a variety of organic compounds. Possible organic compounds include other hydrofluorocarbons or hydrofluoroethers. Typical of other hydrofluorocarbons would be those which are commercially available and could be selected from the list including 1,1,2,2,3-pentafluoropropane (HFC-245ca, 1H-heptafluoropropane (HFC-227ea), 1,1,1,3,3,3-hexafluoropropane (HFC-236fa), 1,1-difluoroethane (HFC-152a) and 2H,3H-decafluoropentane. Typical of the hydrofluoroethers would be mixtures of methylnonafluobutylether and methylnonafluoroisobutylether (the mixture is sold as HFE-7100) and 1,1,2,2-tetrafluoromethyl ether (HFE-254 pc). The composition of the azeotropic mixtures of H FC-245fa/hydrofluorocarbon or hydrofluoroether and H FC-365mfc/hydrofluorocarbon or hydrofluoroether can vary widely. Typical of the ratios of HFC/other component for these compositions are 99-1 weight percent, the more preferred ratio being 99-30 weight percent and the most preferred being 99-50 weight percent.

Preferred imaging reagents are those that, after contacting the residue of a latent biometric, are capable of rendering a visual image of that biometric. Typically, such renditions involve a chemical reaction between the imaging reagent and one or more compounds of the residue wherein the imaging reagent or one or more of its derivatives are converted into a dye that is visibly detectable and/or fluoresces. Preferred imaging reagents include ninhydrin, hydrindantin, 1,8-diazafluoren-9-one, 1,2-indanedione, and derivatives thereof. By "derivate", it is meant a compound that is functionally and/or structurally related to the referenced compound. Derivatives include, but are not necessarily limited to, products or byproducts of a reaction involving the referenced compound.

Developing compositions are preferably formed by first dissolving the desired imaging reagent in a small amount of a starter solvent suitable solvent or solvent blend. Examples of preferred starter solvents for this initial dissolution include trans-dichloroethylene and organic alcohols, preferably methyl or ethyl alcohol. For example, approximately 100 mg of an imaging reagent can be dissolved in 1 mL of ethanol. These "stock" solutions are further diluted with carrier solvents, i.e., $C_3$-$C_4$ hydrofluorocarbon(s), to produce a "working" solutions. The imaging reagents can be present in the working solution over a wide range of concentrations. However, for ease of application, the imaging reagents used in the present invention have concentrations on the order of millimolar (mmol), e.g., concentrations ranging from 0.1 mmol to 200 mmol. A preferred concentration is 0.1 to 30 mmol.

It is noted that the formulations of this invention do not need to use acetic acid to ensure solubility of the imaging reagents as prior art inventions have indicated. This is yet another advantage of this invention, as providing a formulation sans acid yields a formulation with an extended shelf life. In addition, the formulation sans acid also has the advantage of not causing inks to run or ridge patterns to coalesce.

In certain preferred embodiments, the developing composition of the present invention are applied to an article using one of two techniques: (1) "dipping" and (2) aerosol spraying. However, the following description of these two techniques is not intended to suggest or imply that the scope of the invention is limited to only these two techniques. It should be apparent to one skilled in the art that the use of other application techniques, such as atomization where the formulation can be applied via a pump spray bottle is possible.

In the first method, the surface of the article contaminated with the fingerprint is placed into a container having a suitable amount of liquid formulation. The surface of the article is brought into full contact with the formulation. Contact times can vary. It was found that a contact time of 1 second to 120 seconds was acceptable. The most preferred times were 10 seconds to 30 seconds, although other preferred ranges include about 1 to about 15 second and about 2 to about 5 seconds. This time frame produces visualized prints exhibiting good ridge detail and minimizes the potential of obscuring the detail due to solubilization of the deposits on the surface of the article.

In the second method, the formulation is deposited by spraying the imaging reagent on the surface of the article from an aerosol can. The concentration of the imaging reagents is similar to that described above and the dilution caused by adding a propellant into the aerosol can is neglected. Propellants that can be used for this application include nitrogen gas, carbon dioxide gas and hydrofluorocarbon bases which impart suitable pressure to expel the formulation from the canister. Typical of such hydrofluorocarbon gases would be tetrafluoroethane also known as HFC-134a. The use of this fluorocarbon gas is not intended to limit the scope of propellants selected for this application but is used for purposes of demonstration only. The amount of time required for spraying is not critical but should be as short as possible to conserve imaging reagents. Typically spray times of 1-15 seconds are possible with the preferred times of 2-5 seconds being the most preferred. After dipping or spraying is completed, excess imaging reagent can be removed by either dipping the surface of the article into neat carrier fluid or spraying the surface of the article with neat carrier fluid. To complete the process, the surface of the article should be dried to provide optimum viewing of the visualized fingerprint. Drying can be accomplished by allowing the carrier fluid to evaporate by applying heat and moist air at ~100° C. as a means to accelerate the evaporation process. The use of moist air aids in the development of highlight ridge details, particularly in the case where ninhydrin is used as the imaging reagent.

A wide variety of article materials can be used in the present invention. Preferred articles include fibrous textile, nonwoven, or paper, such as those constructed of cellulose, polyester, polyethylene, acrylic, nylon, polyurethane, olefin, or some combination thereof. Examples of preferred articles include, but are not limited to, photocopier paper, file card paper stock, newspaper, manila envelopes, brown paper bags, newsprint, both black and white and colored, cardboard, Post-it Notes®, a product of the 3M company, and paper currency such as banknotes.

Another objective met by the formulations of this invention is to provide an imaging reagent carrier which does not cause inks to streak. In accordance with this objective, the above formulations were tested against the following inks: a red, black or blue ball point pen (Papermate), Flair pens, gel pens (Avery) and Sharpie pens. There was no streaking or running observed with any of the formulations.

EXAMPLES

In order that the invention may be more readily understood, reference is made to the following examples which are intended to be illustrative of the invention, but are not intended to limit the scope of the invention.

Comparative Example 1

This example describes the preparation of a standard formulation using the known HFC-4310mee as carrier which serves as a reference for comparing fingerprint imaging quality.
Ninhydrin (5 g, 0.0281 mol) was dissolved in 15 mL of ethanol containing 5 mL of ethyl acetate and 10 mL of acetic acid. After a homogeneous solution was obtained, it is diluted with 1 L of HFC-4310mee to produce the final formulation used for comparison.

Example 2

This example describes the preparation of a novel formulation according to the present invention.
Ninhydrin (0.1079 g, $6.05 \times 10^{-4}$ mol) was dissolved in 0.75 mL of ethanol. After the ninhydrin dissolved, it was diluted with 30 mL of HFC-245fa. A homogeneous solution was obtained. This solution was used for developing fingerprints on various articles.

Example 3

This example utilizes all components as described in Example 1 and is used to demonstrate that no deleterious results are obtained using the hydrofluorocarbons of this invention.
Ninhydrin (0.2437 g, $1.367 \times 10^{-3}$ mol) was dissolved in 2.25 mL of ethanol containing 0.1 mL of ethyl acetate and 0.25 mL of acetic acid. After the ninhydrin was dissolved, it was diluted with 50 mL of HFC-245fa. A homogeneous solution was obtained. This solution was used for developing fingerprints on various articles as described below.

Example 4

This example demonstrates the use of a different HFC in accordance with this patent.
Ninhydrin (0.1431 g, $8.03 \times 10^{-4}$ mol) were dissolved in 0.75 mL of ethanol. After the ninhydrin was dissolved, this solution was diluted with 30 mL of HFC-365mfc. A homogeneous solution was obtained. This solution was used for developing fingerprints on various articles as described below.

Example 5

This example is used to demonstrate that a different imaging reagent is soluble in HFCs.
DFO (0.0344 g, $1.88 \times 10^{-4}$ mol) was dissolved in 1 mL of ethanol. The dissolution under these conditions did not go to completion. Un-dissolved DFO was removed by filtration and the remaining homogeneous solution diluted with 30 mL of HFC-245fa. This solution was used for developing fingerprints on various articles as described below.

Example 6

This was a duplication of Example 5 with the exception that 0.25 mL of acetic acid was utilized to affect complete dissolution of the DFO reagent. A homogeneous solution was obtained.

Example 7

The formulation of this example was identical to that described in Example 6 except that the HFC was changed to HFC-365mfc. A homogeneous solution was obtained.

Example 8

The formulation of this example was identical to Example 6 except that a 50/50 mix of HFC-246fa and HFC-365mcf (by volume) was used as the carrier solvent. A homogeneous solution was obtained.

Example 9

The formulation of this example was similar to that described in Example 2 except that the carrier solvent was a 9% by volume mix of trans-1,2-dichloroethane and HFC-245fa. A homogeneous solution was obtained.

Example 10

The formulation of this example was similar to that described in Example 2 except that the carrier solvent was a 70/30 mixture of HFC-245fa and HFC-4310mee (by volume). A homogeneous solution was obtained.

Example 11

The formulation of this example was similar to that described in Example 10 except a 50/50 mix of HFC-245fa and HFC-4310mee (by volume) was used as the carrier solvent. A homogeneous solution was obtained.

Example 12

The following examples as directed towards the preparation of an aerosol can containing the following formulation.

Ninhydrin (0.7338 g, $4.12 \times 10^{-3}$ mol) was dissolved in 5 mL of ethanol. This imaging reagent solution was added to 200 mL of HFC-245fa and the contents placed into a 300 ml aerosol can. HFC-134a (30 g) was added as propellant for the formulation.

A homogeneous solution was obtained. This mixture was used to spray develop latent fingerprints on various articles.

The following examples describe the development of latent fingerprints with the formulations of this invention.

Example 13

A piece of photocopier paper having a latent print residue was immersed in the formulation described in Example 2 for 10 seconds, then rinsed with HFC-245fa by immersion for 5 seconds then dried at about 100° C. in moist air. The result from this solution was a highly visible purple fingerprint with well defined ridges.

Example 14

This example followed the procedure as described in Example 13 except that the article was changed to file card stock. The result from this solution was a highly visible purple fingerprint with well defined ridges.

Example 15

This example followed the procedure as described in Example 13 except that the article was changed to black and white newspaper print. The result from this solution was a highly visible purple fingerprint with well defined ridges.

Example 16

This example followed the procedure as described in Example 13 except that the article was changed to color newspaper print. The result from this solution was a highly visible purple fingerprint with well defined ridges.

Example 17

This example followed the procedure as described in Example 13 except that the article was changed to a manila envelop. The result from this solution was a highly visible purple fingerprint with well defined ridges.

Example 18

This example followed the procedure as described in Example 13 except that the article was changed to a brown paper bag. The result from this solution was a highly visible purple fingerprint with well defined ridges.

Example 19

This example followed the procedure as described in Example 13 except that the article was changed to cardboard. The result from this solution was a highly visible purple fingerprint with well defined ridges.

Example 20

This example followed the procedure as described in Example 13 except that the article was changed to yellow Post-it notes. The result from this solution was a highly visible purple fingerprint with well defined ridges.

Example 21

This example followed the procedure as described in Example 13 except that the article was changed to paper money. The result from this solution was a highly visible purple fingerprint with well defined ridges.

Example 22

Utilizing the aerosol formulation of Example 12, a piece of photocopier paper was sprayed for 5 seconds with the developer formulation followed by a second rinse in neat HFC-245fa. Upon drying at about 100° C. in moist air, well developed, highly visible purple fingerprint ridges were obtained.

Example 23

This example followed the procedure as described in Example 22 except that the article was changed to file card stock. The result from this solution was a highly visible purple fingerprint with well defined ridges.

Example 24

This example followed the procedure as described in Example 22 except that the article was changed to black and white newspaper print. The result from this solution was a highly visible purple fingerprint with well defined ridges.

Example 25

This example followed the procedure as described in Example 22 except that the article was changed to color newspaper print. The result from this solution was a highly visible purple fingerprint with well defined ridges.

Example 26

This example followed the procedure as described in Example 22 except that the article was changed to a manila envelop. The result from this solution was a highly visible purple fingerprint with well defined ridges.

Example 27

This example followed the procedure as described in Example 22 except that the article was changed to a brown paper bag. The result from this solution was a highly visible purple fingerprint with well defined ridges.

Example 28

This example followed the procedure as described in Example 22 except that the article was changed to cardboard.

The result from this solution was a highly visible purple fingerprint with well defined ridges.

Example 29

This example followed the procedure as described in Example 22 except that the article was changed to yellow Post-it notes. The result from this solution was a highly visible purple fingerprint with well defined ridges.

Example 30

This example followed the procedure as described in Example 22 except that the article was changed to paper money. The result from this solution was a highly visible purple fingerprint with well defined ridges.

Example 31

This example demonstrates the use of a mixed carrier solvent prepared from an HFC and an HFE.

A 50/50 mix by volume of HFC-245fa and HFE-7100 was prepared. To 50 mL of this mixture was added ninhydrin (0.1164 g, $6.6 \times 10^{-4}$ mol) dissolved in 0.75 mL of ethanol. Photocopier paper, manila envelopes and newspaper print having a latent fingerprint were immersed into this formulation for 10 seconds, then dried at 100° C. containing moist air. In all cases, the fingerprint ridges were well developed.

Example 32

This example is analogous to Example 31 except that the mix of HFC-245fa/HFE7100 was changed to 70/30. All fingerprints were well developed.

Example 33

This example demonstrates the use of an HFC with yet another co-solvent.

Ninhydrin (0.1594 g, $8.9 \times 10^{-4}$ mol) was dissolved in 0.73 mL of ethanol. This solution was added to 30 mL of a co-solvent solution comprised of HFC-245fa and trans-dichloroethylene (9 wt %). Latent fingerprints were obtained from photocopied paper.

Example 34

This example describes the results of exposing various inks to the solvents of this invention.

The following ink samples were scribed onto photocopier paper: black or blue ball point pen (Papermate), Flair pens, gel pens (Avery) and Sharpie pens. The paper was immersed into the formulation described in Example 2 for 10 seconds. No streaking of the inks occurred. Repeated immersion was conducted for an additional 12 cycles. No streaking of any of the inks occurred.

The present invention provides an environmentally sound solution to transporting fingerprint imaging reagents to various articles. Various modifications of the preferred embodiments may occur to those skilled in the art without departing from the spirit and scope of this invention as defined by the following claims.

What is claimed is:

1. A composition comprising:
   a. an imaging reagent selected from the group consisting of hydrindantin, 1,2-indanedione, ninhydrin and 1,8-diazafluoren-9-one; and
   b. a carrier solvent comprising at least one pentafluoropropane.
2. The composition of claim 1 wherein said carrier solvent comprises at least about 50 weight percent of said pentafluoropropane.
3. The composition of claim 1 wherein said carrier solvent comprises at least about 70 weight percent of said pentafluoropropane.
4. The composition of claim 1 wherein said carrier solvent comprises at least about 99 weight percent of said pentafluoropropane.
5. The composition of claim 1 wherein said pentafluoropropane is selected from the group consisting of 1,1,1,3,3-pentafluoropropane; 1,1,2,2,3-pentafluoropropane; and mixtures thereof.
6. The composition of claim 1 wherein said carrier solvent comprises a mixture of 1,1,1,3,3-pentafluorobutane and 1,1,1,3,3-pentafluoropropane.
7. The composition of claim 1 wherein said carrier solvent comprises an azeotropic mixture of said at least one pentafluoropropane and one or more organic compounds.
8. The composition of claim 1 further comprising a co-solvent selected from decafluoropentane, methylnonafluorobutylether, methylnonafluoroisobutylether, and mixtures thereof.
9. The composition of claim 1 wherein said imaging reagent is ninhydrin.
10. The composition of claim 1 wherein said imaging reagent is 1,8-diazafluoren-9-one.
11. The composition of claim 1 wherein said imaging reagent is hydrindantin.
12. The composition of claim 1 wherein said imaging reagent is 1,2-indanedione.
13. A composition comprising:
   c. an imaging reagent selected from the group consisting of hydrindantin, 1,2-indanedione, ninhydrin and 1,8-diazafluoren-9-one; and
   d. a carrier solvent comprising at least one $C_3$-$C_4$ hydrofluorocarbon, wherein the carrier solvent comprises at least about 99 weight percent of said $C_3$-$C_4$ hydrofluorocarbons.
14. A composition comprising:
   e. an imaging reagent selected from the group consisting of hydrindantin, 1,2-indanedione, ninhydrin and 1,8-diazafluoren-9-one; and
   f. a carrier solvent comprising at least one $C_3$-$C_4$ hydrofluorocarbon selected from the group consisting of 1,1,1,3,3-pentafluoropropane; 1,1,2,2,3-pentafluoropropane; 1,1,1,3,3,3-hexafluoropropane; 1,1,1,2,3,3,3-heptafluoropropane; and mixtures thereof.
15. A composition comprising:
   g. an image reagent comprising hydrindantin; and
   h. a carrier solvent comprising at least one $C_3$-$C_4$ hydrofluorocarbon.
16. A sprayable composition comprising the composition of claim 1.
17. The sprayable composition of claim 16 further comprising a propellant.
18. The sprayable composition of claim 17 wherein the propellant comprises nitrogen gas or carbon dioxide gas.
19. The sprayable composition of claim 17 wherein the propellant comprises a hydrofluorocarbon.
20. The sprayable composition of claim 19 wherein the hydrofluorocarbon comprises HFC-134a.
21. The sprayable composition of claim 16 in the form of an aerosol.

* * * * *